United States Patent
Tian et al.

(10) Patent No.: US 11,940,508 B1
(45) Date of Patent: Mar. 26, 2024

(54) MAGNETIC PARTICLE IMAGING (MPI) AND FLUORESCENCE MOLECULAR TOMOGRAPHY (FMT)-FUSED MULTIMODAL IMAGING SYSTEM FOR SMALL ANIMAL

(71) Applicant: Beijing University of Aeronautics and Astronautics, Beijing (CN)

(72) Inventors: Jie Tian, Beijing (CN); Lishuang Guo, Beijing (CN); Jiangang Liu, Beijing (CN); Yu An, Beijing (CN)

(73) Assignee: Beijing University of Aeronautics and Astronautics, Beijing (CN)

( * ) Notice: Subject to any disclaimer, the term of this patent is extended or adjusted under 35 U.S.C. 154(b) by 0 days.

(21) Appl. No.: 18/500,093

(22) Filed: Nov. 1, 2023

(30) Foreign Application Priority Data

Feb. 7, 2023 (CN) .......................... 202310070551.4

(51) Int. Cl.
| | |
|---|---|
| *G01R 33/12* | (2006.01) |
| *A61B 5/00* | (2006.01) |
| *A61B 5/0515* | (2021.01) |
| *G01R 33/00* | (2006.01) |
| *G01R 33/10* | (2006.01) |
| *G01R 33/385* | (2006.01) |

(52) U.S. Cl.
CPC ........ *G01R 33/1276* (2013.01); *A61B 5/0073* (2013.01); *A61B 5/0515* (2013.01); *G01R 33/0023* (2013.01); *G01R 33/10* (2013.01); *G01R 33/385* (2013.01)

(58) Field of Classification Search
CPC ....................... G01R 33/1276; G01R 33/0023; G01R 33/10; G01R 33/385; A61B 5/0515; A61B 5/0071; A61B 5/0073
See application file for complete search history.

(56) References Cited

U.S. PATENT DOCUMENTS 11,776,174 B1 * 10/2023 Tian ...................... G06T 7/0012
382/131

FOREIGN PATENT DOCUMENTS

| CA | 2428462 A1 | 5/2002 |
|---|---|---|
| CN | 114376550 A | 4/2022 |
| CN | 114581553 A | 6/2022 |
| CN | 115153490 A | 10/2022 |
| EP | 1898206 A1 | 3/2008 |
| WO | 2009129137 A1 | 10/2009 |

* cited by examiner

*Primary Examiner* — Rishi R Patel
(74) *Attorney, Agent, or Firm* — Bayramoglu Law Offices LLC (57) ABSTRACT

A magnetic particle imaging (MPI) and fluorescence molecular tomography (FMT)-fused multimodal imaging system and method for a small animal are provided. The multimodal imaging system includes an image processing module, a display module, a control module, an object table, a gradient coil, a driving coil, a reception coil, a fluorescence camera, and a light source module, where the gradient coil includes a first rounded rectangular coil and a second rounded rectangular coil; the driving coil includes a third rounded rectangular coil, a fourth rounded rectangular coil, and a fifth rounded rectangular coil; and the reception coil is a circular coil.

13 Claims, 5 Drawing Sheets

FIG. 1

| S100 | Inject a magnetic-nano and optical-fused probe into a body of a target object |
|---|---|
| S200 | Generate a static FFL in a gradient coil |
| S300 | Control translation and rotation of the FFL in a space, and scan-image the target object on an object table |
| S400 | Reconstruct a nonlinear response signal received by a reception coil to generate an MPI cross-sectional image |
| S500 | Acquire and preprocess a fluorescence image of a surface of the target object |
| S600 | Perform FMT reconstruction to acquire a 3D structural fluorescence distribution of a lesion region in the body of the target object |
| S700 | Assign concentration information of magnetic particles in the MPI cross-sectional image to a grid node of the 3D structural fluorescence distribution, thereby acquiring an image fusion result including the 3D fluorescence distribution, the concentration information of the magnetic particles, and a 3D structure |

MAGNETIC PARTICLE IMAGING (MPI) AND FLUORESCENCE MOLECULAR TOMOGRAPHY (FMT)-FUSED MULTIMODAL IMAGING SYSTEM FOR SMALL ANIMAL

CROSS REFERENCE TO THE RELATED APPLICATIONS

This application is based upon and claims priority to Chinese Patent Application No. 202310070551.4, filed on Feb. 7, 2023, the entire contents of which are incorporated herein by reference.

TECHNICAL FIELD

The present disclosure belongs to the technical field of medical imaging and detection, and in particular relates to a magnetic particle imaging (MPI) and fluorescence molecular tomography (FMT)-fused multimodal imaging system and method for a small animal.

BACKGROUND

Achieving accurate in-vivo imaging and localization of target lesions with high sensitivity and high resolution has always been a research hotspot and challenging issue of clinical detection and diagnosis internationally. As a new type of tracer-based imaging technique, magnetic particle imaging (MPI) offers a three-dimensional (3D) imaging method that is not limited by imaging depth. MPI can accurately localize the detection target by reconstructing the spatial concentration distribution of superparamagnetic iron oxide (SPIO) nanoparticles based on the nonlinear magnetization response of the harmless-to-body SPIO nanoparticles to a magnetic field. In addition, MPI is free from harmful radiation and background signal interference. The signal intensity is directly related to the concentration of the tracer, so the iron content in the magnetic particles can be quantified. At present, MPI has been applied in basic research fields such as cell tracking, angiography, and infection imaging, and has great potential in medical applications.

However, MPI cannot display the anatomical structure of the detected object and has low resolution, making it hard to observe lesions smaller than those on the submillimeter scale, such as minimal tumors and diseased tissues. The existing fluorescence imaging technique relies on a fluorescence probe labeling method to track molecular and protein changes in biological tissues and cells. The fluorescence imaging technique can acquire the anatomical structure information of tissues, and has the advantages of intuitive imaging effect and high resolution. Fluorescence molecular tomography (FMT) can acquire the distribution of fluorescent molecules in a 3D space, but it is limited by tissue scattering and cannot accurately reflect molecular quantitative information. However, the fusion of MPI and FMT can help to achieve 3D information visualization of lesions with high resolution and high sensitivity.

SUMMARY

The present disclosure aims to solve the above-mentioned problems existing in the prior art, that is, magnetic particle imaging (MPI) has low resolution and fluorescence molecular tomography (FMT) has insufficient field of view, thereby resulting in low accuracy of image reconstruction. For this purpose, the present disclosure proposes an MPI and FMT-fused multimodal imaging system for a small animal. The multimodal imaging system includes an image processing module, a display module, a control module, an object table, a gradient coil, a driving coil, a reception coil, a fluorescence camera, and a light source module, where the gradient coil includes a first rounded rectangular coil and a second rounded rectangular coil; the first rounded rectangular coil and the second rounded rectangular coil are located on a same horizontal plane that serves as a first horizontal plane; the first rounded rectangular coil and the second rounded rectangular coil are arranged with respective long sides opposite, short sides flush, and axes parallel, and are symmetrically distributed at two sides of a longitudinal axis at a center of the object table; and the gradient coil is configured to construct a static field free line (FFL), such that magnetic particles around the FFL are saturated to form a gradient field in a space;

the driving coil includes a third rounded rectangular coil, a fourth rounded rectangular coil, and a fifth rounded rectangular coil; the third rounded rectangular coil, the fourth rounded rectangular coil, and the fifth rounded rectangular coil are located on a same horizontal plane that serves as a second horizontal plane; the second horizontal plane is parallel to the first horizontal plane; the third rounded rectangular coil, the fourth rounded rectangular coil, and the fifth rounded rectangular coil are arranged with respective long sides parallel and short sides flush; a center of the third rounded rectangular coil and the center of the object table are located on a same longitudinal axis; the fourth rounded rectangular coil and the fifth rounded rectangular coil are located at two sides of the third rounded rectangular coil, and have a same distance to the third rounded rectangular coil; and the driving coil is configured to counteract a magnetic field of the gradient coil so as to control the FFL to make translational motion;

the reception coil is a circular coil provided directly below the object table and above the gradient coil; and the reception coil is configured to acquire a nonlinear response signal of the magnetic particles;

the fluorescence camera is provided directly above the object table to perform real-time imaging of a target object placed on the object table;

the light source module is fixed at a periphery of a fluorescence lens of the fluorescence camera to control an imaging mode of the fluorescence camera; and the image processing module is configured to process an image acquired by the real-time imaging of the fluorescence camera as a first image, process and reconstruct the nonlinear response signal acquired by the reception coil as a second image, and fuse the first image and the second image to generate a final imaging result.

In some preferred implementations, the multimodal imaging system takes a direction of the longitudinal axis at the center of the object table as a z-direction and a left-right direction of the longitudinal axis at the center of the object table as an x-direction.

In some preferred implementations, a fluorescence acquisition module and the center of the object table are located on a same perpendicular line; and the light source module is a circular light source with a white light source and fluorescent light source integrated imaging mode.

The object table is able to move up and down and rotate in the z-direction.

In some preferred implementations, the gradient coil is configured to construct the static FFL by applying currents of equal magnitude and opposite directions to the first rounded rectangular coil and the second rounded rectangular coil.

A second aspect of the present disclosure proposes an MPI and FMT-fused multimodal imaging method for a small animal, based on the MPI and FMT-fused multimodal imaging system for a small animal, and including:

S100: fixing a target object to the object table, and injecting a magnetic-nano and optical-fused probe into a body of the target object;

S200: applying the currents to the gradient coil to generate the static FFL;

S300: applying a high-frequency excitation current to the driving coil, changing a current ratio between the gradient coil and the driving coil, and controlling translation and rotation of the FFL in the space, thereby scan-imaging the target object on the object table;

S400: decoding and reconstructing the nonlinear response signal acquired by the reception coil to generate an MPI cross-sectional image including particle concentration information at different depth positions;

S500: performing, by the fluorescence camera, grayscale subtraction between an acquired original fluorescence signal and a previously acquired background signal to generate a fluorescence image of a surface of the target object; and preprocessing the fluorescence image of the surface of the target object through enhancement and denoising to generate a preprocessed fluorescence image;

S600: extracting a position of magnetic particles in the MPI cross-sectional image and concentration information of the magnetic particles at the position; registering, based on a fixed registration reference point, the MPI cross-sectional image into a 3D grid space of computed tomography (CT) as a prior region for FMT reconstruction; and performing, in the prior region for FMT reconstruction, FMT reconstruction on the preprocessed fluorescence image to acquire a 3D structural fluorescence distribution of a lesion region in the body of the target object; and S700: assigning the concentration information of the magnetic particles in the MPI cross-sectional image to a grid node of the 3D structural fluorescence distribution, thereby acquiring an image fusion result including the 3D fluorescence distribution, the concentration information of the magnetic particles, and a 3D structure.

In some preferred implementations, the preprocessing the fluorescence image of the surface of the target object through enhancement and denoising to generate a preprocessed fluorescence image includes:

enhancing the fluorescence image of the surface of the target object through a segmented linear grayscale transformation method, and denoising the fluorescence image of the surface of the target object through a bilateral Gaussian filtering method, thereby acquiring a high-contrast fluorescence image as the preprocessed fluorescence image.

In some preferred implementations, the 3D structural fluorescence distribution of the lesion region in the body of the target object is acquired by:

constructing an FMT reconstruction model, and performing reverse solving as follows:

$$AX = \Phi$$

where, A denotes a forward system matrix; X denotes a fluorescent molecule distribution to be solved; and (I) denotes a surface fluorescence signal;

converting the reverse solving problem into a least squares problem:

$$\min_X E(X) = \|AX - \Phi\|_2^2$$

where, E (X) denotes an optimization function;

where, when the least squares problem is solved, due to an ill-conditioned and ill-posed nature of the system matrix A, an L1 norm constraint is added:

$$\min_X E(x) = \|AX - \Phi\|_2^2 + \lambda\|X\|_1$$

where, $\lambda$ denotes a regularization parameter; and solving the least squares problem with the L1 norm constraint through an oblique projection matching pursuit method, thereby acquiring the 3D structural fluorescence distribution of the lesion region in the body of the target object.

In some preferred implementations, the solving the least squares problem with the L1 norm constraint through an oblique projection matching pursuit method, thereby acquiring the 3D structural fluorescence distribution of the lesion region in the body of the target object includes:

performing a pre-selection process: selecting a node with an intensity greater than a set intensity threshold from a fluorescence signal $\Phi$; adding the node to a pre-constructed pre-selected set $E_t$; and calculating an oblique projection operator and a complementary projection operator of each node in the pre-selected set;

where, the oblique projection operator and the complementary projection operator are expressed as follows:

$$P_{E_t} = A_{E_t} A_{E_t}^+$$

$$P_{E_t}^\perp = I - P_{E_t}$$

where, $A_{E_t}$ denotes a column corresponding to the pre-selected set $E_t$ in the system matrix A; $A_{E_t}^+$ denotes a pseudo inverse of $A_{E_t}$; $P_{E_t}$ denotes a projection operator in span($A_{E_t}$), namely the oblique projection operator; $P_{E_t}^\perp$ denotes a projection operator in an orthogonal complementary space of span($A_{E_t}$), namely the complementary projection operator; and I denotes an identity matrix;

performing a cyclic iteration process: selecting a column with a strongest correlation with a residual of a previous iteration among remaining columns in the system matrix A, and adding a number of the selected column to a support set T, where the correlation is calculated by an inner product of the column and the residual; and the support set includes some column elements that meet a condition in the system matrix, and is set as an empty matrix before a first iteration; and calculating, based on the support set, a temporary solution X and a residual $r_k$:

$$X = (P_{E_t}^\perp A_T)^\dagger \Phi$$

$$r^k = \Phi - A_T X$$

where, A T denotes an expansion of elements in the system matrix A corresponding to the support set before a current iteration; and exiting the iteration when an iteration termination condition is met, that is, when the residual of the current iteration is less than a preset threshold s; and outputting the temporary solution and the support set for the current iteration.

The present disclosure has following beneficial effects:

The present disclosure can simultaneously acquire images of the concentration distribution of magnetic nanoparticles and the distribution of fluorescent molecules, achieving rapid fusion and visualization of "function-molecule-structure" imaging information, and improving the accuracy of image reconstruction.

The present disclosure can simultaneously acquire the concentration distribution of magnetic nanoparticles and fluorescent molecules. In this way, the present disclosure provides tissue depth information for FMT and anatomical structure information for MPI. By integrating the advantages of FMT and MPI, the present disclosure improves detection accuracy and achieves high-resolution and high-sensitivity visualization of 3D lesion information.

BRIEF DESCRIPTION OF THE DRAWINGS

Other features, objectives and advantages of the present disclosure will become more apparent upon reading the detailed description of the non-restrictive embodiments made below with reference to the drawings.

Reference Numerals: 11. object table; 12. gradient coil; 13. driving coil; 14. reception coil; 15. control module; 16. fluorescence camera; 17. light source module; 18. image processing module; and 19. display module.

DETAILED DESCRIPTION OF THE EMBODIMENTS

In order to make the objectives, technical solutions, and advantages of the embodiments of the present disclosure clearer, the technical solutions in the embodiments of the present disclosure will be clearly and completely described below in conjunction with the drawings in the embodiments of the present disclosure. Apparently, the described embodiments are some, rather than all of the embodiments of the present disclosure. All other embodiments obtained by those skilled in the art based on the embodiments of the present disclosure without creative efforts shall fall within the protection scope of the present disclosure.

The present disclosure will be further described in detail below in conjunction with the drawings and embodiments. It may be understood that the specific embodiments described herein are merely intended to explain the related invention, rather than to limit the present disclosure. It should be noted that the embodiments in the present disclosure and features in the embodiments may be combined with each other in a non-conflicting situation.

Figure 1:
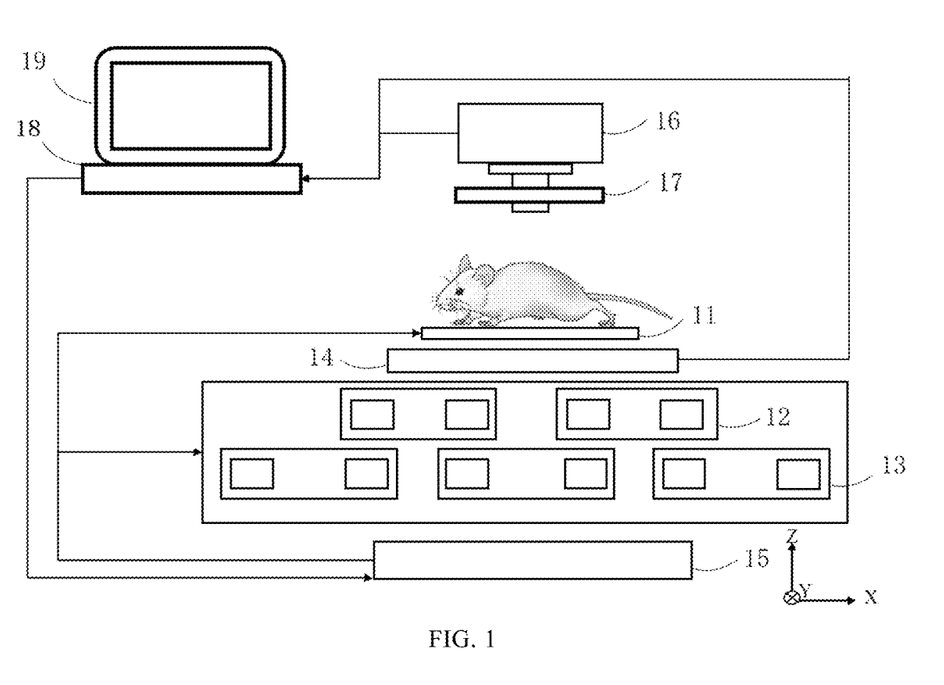
FIG. 1 is a block diagram of a magnetic particle imaging (MPI) and fluorescence molecular tomography (FMT)-fused multimodal imaging system for a small animal according to an embodiment of the present disclosure.

The present disclosure proposes a magnetic particle imaging (MPI) and fluorescence molecular tomography (FMT)-fused multimodal imaging system for a small animal. As shown in FIG. 1, the multimodal imaging system includes an image processing module, a display module, a control module, an object table, a gradient coil, a driving coil, a reception coil, a fluorescence camera, and a light source module.

The gradient coil includes a first rounded rectangular coil and a second rounded rectangular coil. The first rounded rectangular coil and the second rounded rectangular coil are located on a same horizontal plane that serves as a first horizontal plane. The first rounded rectangular coil and the second rounded rectangular coil are arranged with respective long sides opposite, short sides flush, and axes parallel, and are symmetrically distributed at two sides of a longitudinal axis at a center of the object table. The gradient coil is configured to construct a static field free line (FFL), such that magnetic particles around the FFL are saturated to form a gradient field in a space.

The driving coil includes a third rounded rectangular coil, a fourth rounded rectangular coil, and a fifth rounded rectangular coil. The third rounded rectangular coil, the fourth rounded rectangular coil, and the fifth rounded rectangular coil are located on a same horizontal plane that serves as a second horizontal plane. The second horizontal plane is parallel to the first horizontal plane. The third rounded rectangular coil, the fourth rounded rectangular coil, and the fifth rounded rectangular coil are arranged with respective long sides parallel and short sides flush; a center of the third rounded rectangular coil and the center of the object table are located on a same longitudinal axis. The fourth rounded rectangular coil and the fifth rounded rectangular coil are located at two sides of the third rounded rectangular coil, and have a same distance to the third rounded rectangular coil. The driving coil is configured to counteract a magnetic field of the gradient coil so as to control the FFL to make translational motion.

The reception coil is a circular coil provided directly below the object table and above the gradient coil. The reception coil is configured to acquire a nonlinear response signal of the magnetic particles.

The fluorescence camera is provided directly above the object table to perform real-time imaging of a target object placed on the object table.

The light source module is fixed at a periphery of a fluorescence lens of the fluorescence camera to control an imaging mode of the fluorescence camera.

The image processing module is configured to process an image acquired by the real-time imaging of the fluorescence camera as a first image, process and reconstruct the nonlinear response signal acquired by the reception coil as a second image, and fuse the first image and the second image to generate a final imaging result.

To more clearly explain the MPI and FMT-fused multimodal imaging system for a small animal in the present disclosure, the modules in the embodiment of the present disclosure are described in detail below.

As shown in FIG. 1, the modules of the MPI and FMT-fused multimodal imaging system for a small animal are described below.

The object table 11 is a circular table for carrying the target object. In the present disclosure, the multimodal imaging system takes a direction of the longitudinal axis at the center of the object table as a z-direction and a left-right direction of the longitudinal axis at the center of the object table as an x-direction, as shown in FIG. 1. The object table is able to move up and down and rotate in the z-direction.

The gradient coil 12 includes a first rounded rectangular coil and a second rounded rectangular coil. The first rounded rectangular coil and the second rounded rectangular coil are located on a same horizontal plane that serves as a first horizontal plane. The first rounded rectangular coil and the second rounded rectangular coil are arranged with respective long sides opposite, short sides flush, and axes parallel, and are symmetrically distributed at two sides of a longitudinal axis at a center of the object table. In other embodiments, the first rounded rectangular coil and the second rounded rectangular coil of the gradient coil can be replaced with a permanent magnet group, especially in a small-scale MPI system. The advantage of the permanent magnet group is that it is compact and easy to build, without considering heat dissipation and power loss, and is prone to generating a gradient field, thereby significantly improving the performance of the scanner. In a large-scale MPI system, electromagnetic coils are preferred, as they have the advantages of flexible control and the ability to change the size of the magnetic field according to experimental requirements. However, they raise high requirements for timely heat dissipation and voltage.

The gradient coil is configured to construct a static FFL, such that magnetic particles around the FFL are saturated to form a gradient field in a space. Specifically:

Currents of equal magnitude and opposite directions are applied to the first rounded rectangular coil and the second rounded rectangular coil. The opposite currents generate a static FFL, which adapts to the reference height of the FFL in different application scenarios. The gradient of the magnetic field is adjusted by changing the magnitude of the opposite currents.

The driving coil 13 uses an excitation coil, and includes a third rounded rectangular coil, a fourth rounded rectangular coil, and a fifth rounded rectangular coil. The third rounded rectangular coil, the fourth rounded rectangular coil, and the fifth rounded rectangular coil are located on a same horizontal plane that serves as a second horizontal plane. The second horizontal plane is parallel to the first horizontal plane; the third rounded rectangular coil, the fourth rounded rectangular coil, and the fifth rounded rectangular coil are arranged with respective long sides parallel and short sides flush. A center of the third rounded rectangular coil and the center of the object table are located on a same longitudinal axis. The fourth rounded rectangular coil and the fifth rounded rectangular coil are located at two sides of the third rounded rectangular coil, and have a same distance to the third rounded rectangular coil.

The driving coil is configured to counteract a magnetic field of the gradient coil so as to control the FFL to make translational motion. Specifically, currents (i.e., high-frequency excitation currents) of different frequencies and directions are applied to the third rounded rectangular coil, the fourth rounded rectangular coil, and the fifth rounded rectangular coil, and the current ratio to the gradient coil is adjusted so as to control the space movement (i.e. translation and rotation) of the FFL.

The reception coil 14 is preferably a circular coil made by winding a litz wire. It is provided directly below the object table and above the gradient coil, and is configured to acquire and send a nonlinear response signal of the magnetic particles to the image processing module.

The fluorescence camera 16 is provided directly above the object table to perform real-time imaging of a target object placed on the object table. The fluorescence camera and the object table are located on a longitudinal axis, and the fluorescence camera is provided with a fluorescence lens for adjusting the field of view of targets of different sizes.

The light source module 17 is fixed at a periphery of the fluorescence lens of the fluorescence camera. The fluorescence acquisition module and the center of the object table are located on a same perpendicular line. The light source module is a circular light source with a white light source and fluorescent light source integrated imaging mode. The light source module is configured to control an imaging mode of the fluorescence camera and acquire a white light image and a fluorescence image.

The image processing module 18 is configured to process an image acquired by the real-time imaging of the fluorescence camera as a first image, process and reconstruct the nonlinear response signal acquired by the reception coil as a second image, and fuse the first image and the second image to generate a final imaging result.

The display module 19 is configured to visualize the final imaging result generated by the image processing module.

The control module 15 is configured to control changes in the current magnitude and directions of the gradient coil according to set control instructions, control a change in the current ratio of the driving coil, and control the up-down movement and rotation of the object table, such that the FFL is translated and rotated to for layer-by-layer scanning, thereby achieving scanning and imaging of a target region of the target object.

It should be noted that the MPI and FMT-fused multimodal imaging system for a small animal in the above embodiments is only described by taking the division of the above functional modules as an example. In practical applications, the above functions can be completed by different functional modules as required, that is, the modules or steps in the embodiments of the present disclosure are further decomposed or combined. For example, the modules in the above embodiments may be combined into one module, or may be further divided into a plurality of sub-modules to complete all or part of the functions described above. The names of the modules and steps involved in the embodiments of the present disclosure are only for distinguishing each module or step, and should not be regarded as improper limitations on the present disclosure.

Figure 2:
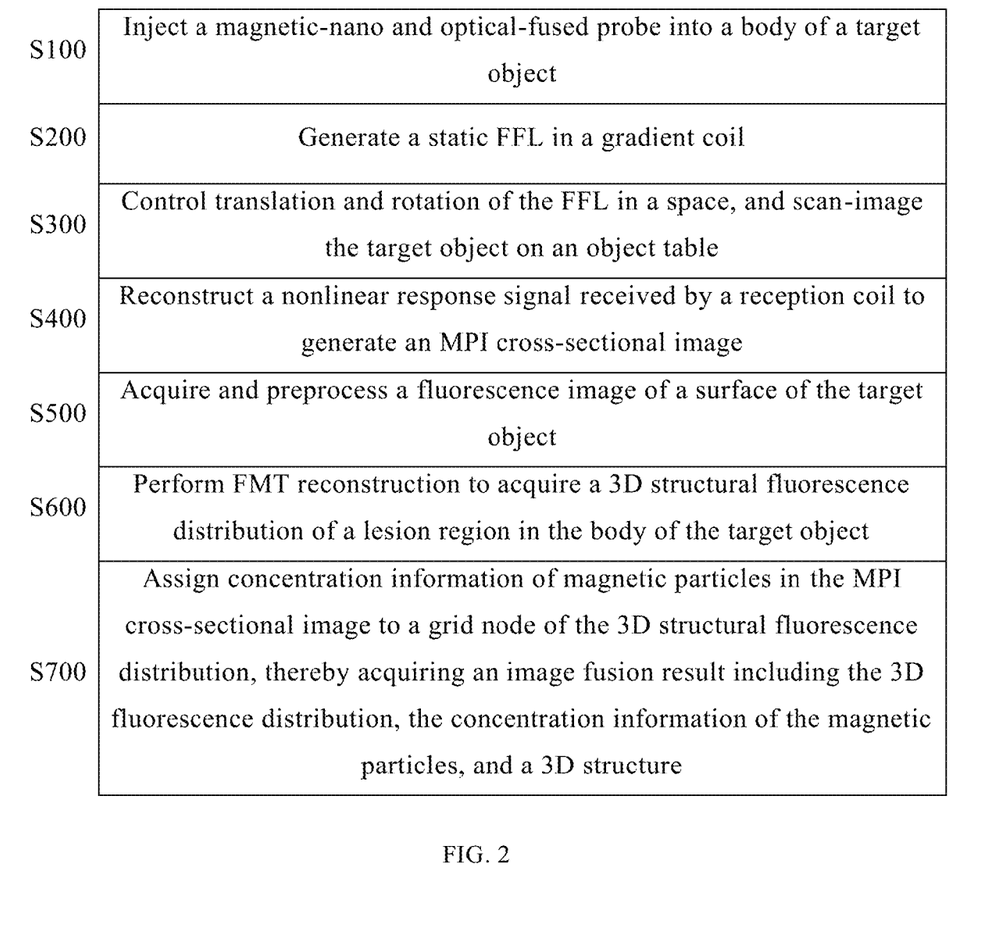
FIG. 2 is a flowchart of an MPI and FMT-fused multimodal imaging method for a small animal according to an embodiment of the present disclosure.

A second embodiment of the present disclosure proposes an MPI and FMT-fused multimodal imaging method for a small animal (a method for scanning and imaging a target region (i.e., lesion region) of a target object through the control module 15). As shown in FIG. 2, the multimodal imaging method is based on the MPI and FMT-fused multimodal imaging system for a small animal, and includes the following steps.

S100. A target object is fixed to the object table, and a magnetic-nano and optical-fused probe is injected into a body of the target object.

In this embodiment, the target object is first fixed on the object table to ensure that it is within a field of view, and the magnetic-nano and optical-fused probe is injected into the body of the target object. In the present disclosure, preferably, the magnetic-nano and optical-fused probe is injected through a tail vein, and the target object is preferably a small animal.

S200. The currents are applied to the gradient coil to generate the static FFL.

In this embodiment, currents of equal magnitude and opposite directions are applied to the first rounded rectangular coil and the second rounded rectangular coil so as to construct the gradient field and generate the static FFL.

S300. A high-frequency excitation current is applied to the driving coil, a current ratio between the gradient coil and the driving coil is changed, and translation and rotation of the FFL in the space are controlled, thereby scan-imaging the target object on the object table;

In this embodiment, the high-frequency excitation current is applied to the driving coil to control an MPI center as an imaging region of the target object. Currents with different frequencies, magnitudes, and ratios are applied to the gradient coil and the driving coil to control the translation and rotation of the FFL in a target space, thereby completing the excitation of the magnetic particles inside the body of the target object. In this way, the scanning and imaging of the target object on the object table is completed.

S400. The nonlinear response signal acquired by the reception coil is decoded and reconstructed to generate an MPI cross-sectional image including particle concentration information at different depth positions.

In this embodiment, the reception coil acquires and transmits a voltage signal corresponding to the concentration of magnetic nanoparticles in the FFL at different positions to the image processing module. The image processing module filters and amplifies the voltage signal, and performs image reconstruction to generate an MPI cross-sectional image. In the present disclosure, preferably, the MPI cross-sectional image is reconstructed through an x-space method.

S500. The fluorescence camera performs grayscale subtraction between an acquired original fluorescence signal and a previously acquired background signal to generate a fluorescence image of a surface of the target object, and the fluorescence image of the surface of the target object is preprocessed through enhancement and denoising to generate a preprocessed fluorescence image.

In this embodiment, the fluorescence camera can acquire the background signal during first use. After the original fluorescence signal is acquired, fluorescence camera automatically sets the subtraction between the background image and the fluorescence image to reduce interference caused by thermal noise of the fluorescence camera.

The fluorescence camera acquires the fluorescence image of the surface of the target object, enhances the fluorescence image of the surface of the target object through a segmented linear grayscale transformation method, and denoises the fluorescence image of the surface of the target object through a bilateral Gaussian filtering method, thereby acquiring a high-contrast fluorescence image as the preprocessed fluorescence image.

S600. A position of magnetic particles in the MPI cross-sectional image and concentration information of the magnetic particles at the position are extracted. Based on a fixed registration reference point, the MPI cross-sectional image is registered into a 3D grid space of computed tomography (CT) as a prior region for FMT reconstruction. In the prior region for FMT reconstruction, FMT reconstruction is performed on the preprocessed fluorescence image to acquire a 3D structural fluorescence distribution of a lesion region in the body of the target object.

In this embodiment, the target depth information and SPIO concentration information are extracted from the reconstructed MPI image. Based on the fixed registration reference point, the MPI cross-sectional image is registered into the CT 3D grid space as a prior region for FMT reconstruction. The registration point includes three fixed reference points in the imaging space, which can be acquired in the FMT mode, MPI mode, and CT mode.

Depth is taken as a prior region for FMT reconstruction, and FMT reconstruction is performed to acquire a 3D structural fluorescence distribution of a lesion region in the body of the target object. This step is specifically as follows.

An optical 3D reconstruction unit is configured to take depth information in the MPI image as prior knowledge and reconstruct a 3D distribution in the body of the target object based on an acquired two-dimensional (2D) fluorescence image and CT structural data. The reverse solution of the FMT reconstruction model is expressed as: AX=Φ, where, A denotes a forward system matrix; X denotes a fluorescent molecule distribution to be solved; and Φ denotes a surface fluorescence signal. Therefore, the FMT reconstruction is a process of solving A and Φ through the known X. The reverse solving problem is converted into a least squares problem:

$$\min_X E(X) = \|AX - \Phi\|_2^2.$$

Due to an ill-conditioned and ill-posed nature of the system matrix A, an L1 norm constraint is added, so the problem is converted into $$\min_X E(X) = \|AX - \Phi\|_2^2 + \lambda \|X\|_1,$$

where λ denotes a regularization parameter, and E(X) denotes an optimization function. To solve the above problem, the present disclosure uses an oblique projection matching pursuit method.

Figure 4:
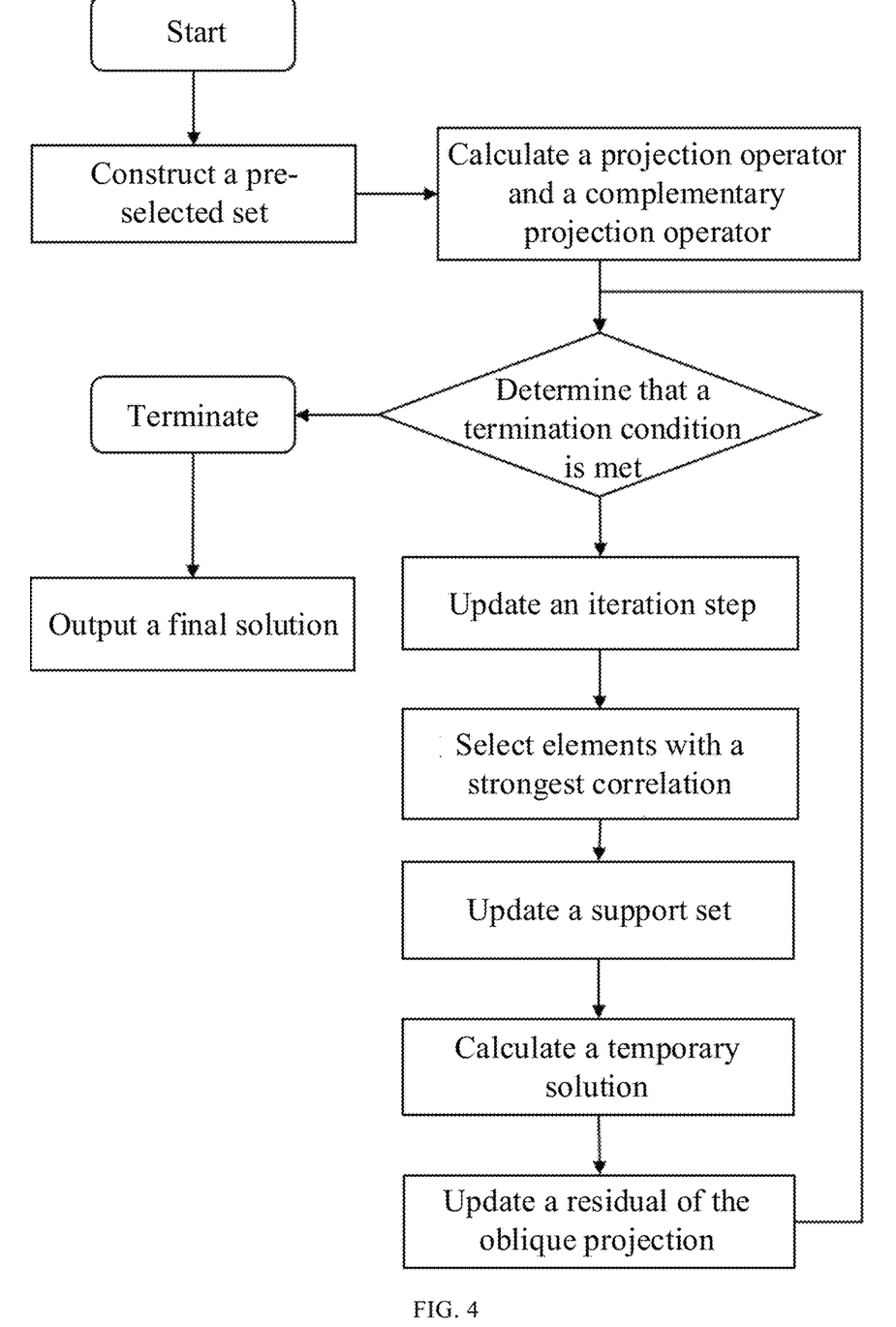
FIG. 4 is a flowchart of an oblique projection matching pursuit method according to an method embodiment of the present disclosure.

The oblique projection matching pursuit method includes a pre-selection process and an iteration process, as shown in FIG. 4. In the pre-selection process, multiple nodes with higher signal intensity in the measured fluorescence signal are selected, and the projection operator and complementary projection operator of the oblique projection of the nodes are calculated. That is, in the pre-selection process, a node with intensity greater than a set intensity threshold is selected from the fluorescence signal Φ and added to the pre-constructed pre-selected set $E_t$, and the projection operator and complementary projection operator of the oblique projection of each node in the pre-selected set are calculated. In the iteration process, correlation calculation, support set update, temporary solution calculation, and residual calculation are carried out in sequence. In the residual calculation step, the oblique projection operator is used. When the iteration termination condition is met, the processing exits the iteration.

The oblique projection operator and the complementary projection operator are expressed as follows:

$$P_{E_t} = A_{E_t} A_{E_t}^+ \tag{1}$$

$$P_{E_t}^\perp = I - P_{E_t} \tag{2}$$

where, $A_{E_t}$ denotes a column corresponding to the pre-selected set $E_t$ in the system matrix A; $A_{E_t}^+$ denotes a pseudo inverse of $A_{E_t}$; $P_{E_t}$ denotes a projection operator in span($A_{E_t}$), namely the oblique projection operator; $P_{E_t}^\perp$ denotes a projection operator in an orthogonal complementary space of span($A_{E_t}$), namely the complementary projection operator; and I denotes an identity matrix.

A cyclic iteration process is performed as follows. A column with a strongest correlation with a residual of a previous iteration is selected among remaining columns in the system matrix A, and a number of the selected column is added to a support set T. The correlation is calculated by an inner product of the column and the residual. The support set includes some column elements that meet a condition in the system matrix, and is set as an empty matrix before a first iteration.

Based on the support set, temporary solution X and residual $r^k$ are calculated:

$$X=(P_{E_t}^\perp A_T)^\dagger)\Phi \quad (3)$$

$$r^k=\Phi-A_T X \quad (4)$$

where, A T denotes an expansion of elements in the system matrix A corresponding to the support set before a current iteration.

The iteration is terminated when an iteration termination condition is met, that is, when the residual of the current iteration is less than a preset threshold ε, and the temporary solution and the support set are output for the current iteration.

S700. The concentration information of the magnetic particles in the MPI cross-sectional image is assigned to a grid node of the 3D structural fluorescence distribution, thereby acquiring an image fusion result including the 3D fluorescence distribution, the concentration information of the magnetic particles, and a 3D structure.

In this embodiment, the particle concentration information in the MPI cross-sectional image is assigned to the grid node of the 3D structural fluorescence distribution so as to acquire the image fusion result including the 3D fluorescence distribution, the magnetic particle concentration information, and the 3D structure.

In summary, in steps S600 and S700, the fluorescence image is fused and registered with the MPI cross-sectional image based on the registration reference point. After the registration, the fluorescence image and the MPI cross-sectional image are simultaneously mapped to the 3D spatial grid of CT for the target object. The FMT reconstruction is performed with the MPI depth information as a prior for fluorescence reconstruction, and particle concentration related information is assigned to the grid node of the fluorescence reconstruction result, thereby acquiring the image fusion result including the 3D fluorescence distribution, the magnetic particle concentration information, and the 3D structure.

Figure 3:
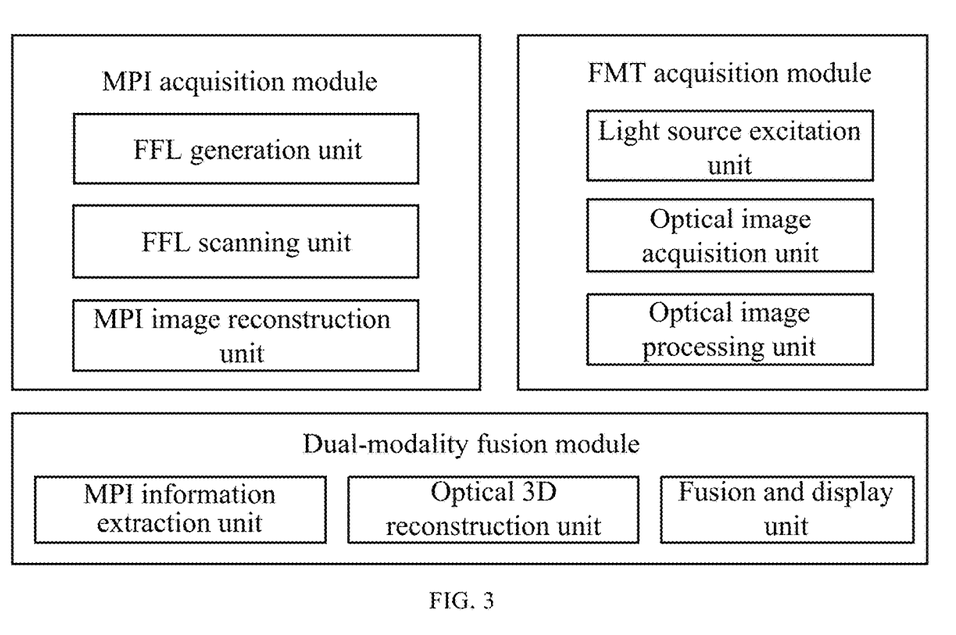
FIG. 3 is a block diagram of modules of the MPI and FMT-fused multimodal imaging system for a small animal according to an embodiment of the present disclosure.

As shown in FIG. 3, based on the multimodal imaging method, the multimodal imaging system includes three major categories of modules, namely an MPI acquisition module, a FMT acquisition module, and a dual-modality module.

The MPI acquisition module includes a FFL generation unit, a FFL scanning unit, and an MPI image reconstruction unit.

The FFL generation unit is configured to apply the currents to the gradient coil to generate the static FFL.

The FFL scanning unit is configured to apply a high-frequency excitation current to the driving coil, change a current ratio between the gradient coil and the driving coil, control translation and rotation of the FFL in the space, and scan the target object on the object table.

The MPI image reconstruction unit is configured to decode and reconstruct the nonlinear response signal acquired by the reception coil to generate an MPI cross-sectional image including particle concentration information at different depth positions.

The FMT acquisition module includes a light source excitation unit, an optical image acquisition unit, and an optical image processing unit.

The light source excitation unit, the optical image acquisition unit, and the optical image processing unit are configured to perform, by the fluorescence camera, grayscale subtraction between an acquired original fluorescence signal and a previously acquired background signal to generate a fluorescence image of a surface of the target object, and preprocess the fluorescence image of the surface of the target object through enhancement and denoising to generate a preprocessed fluorescence image.

The dual-modality fusion module includes an MPI information extraction unit, an optical 3D reconstruction unit, and a fusion and display unit.

The MPI information extraction unit is configured to extract a position of magnetic particles in the MPI cross-sectional image and concentration information of the magnetic particles at the position.

The optical 3D reconstruction unit is configured to register, based on a fixed registration reference point, the MPI cross-sectional image into a 3D grid space of CT as a prior region for FMT reconstruction; and perform, in the prior region for FMT reconstruction, FMT reconstruction on the preprocessed fluorescence image to acquire a 3D structural fluorescence distribution of a lesion region in the body of the target object.

The fusion and display unit is configured to assign the concentration information of the magnetic particles in the MPI cross-sectional image to a grid node of the 3D structural fluorescence distribution, thereby acquiring an image fusion result including the 3D fluorescence distribution, the concentration information of the magnetic particles, and a 3D structure.

Those skilled in the art should clearly understand that, for convenience and brevity of description, reference is made to corresponding processes in the above device embodiments for specific working processes of the method, and details are not described herein again.

A third embodiment of the present disclosure provides an electronic device, including: at least one processor and a memory communicatively connected to the at least one processor, where the memory stores an instruction executable by the processor, and the instruction is executed by the processor to implement the MPI and FMT-fused multimodal imaging method for a small animal.

A fourth embodiment of the present disclosure proposes a computer-readable storage medium, which stores a computer instruction, where the computer instruction is executed by a computer to implement the MPI and FMT-fused multimodal imaging method for a small animal.

Those skilled in the art can clearly understand that, for convenience and brevity of description, reference can be made to a corresponding process in the above method embodiment for specific working processes and related descriptions of the above electronic device and computer-readable storage medium. Details are not described herein again.

Figure 5:
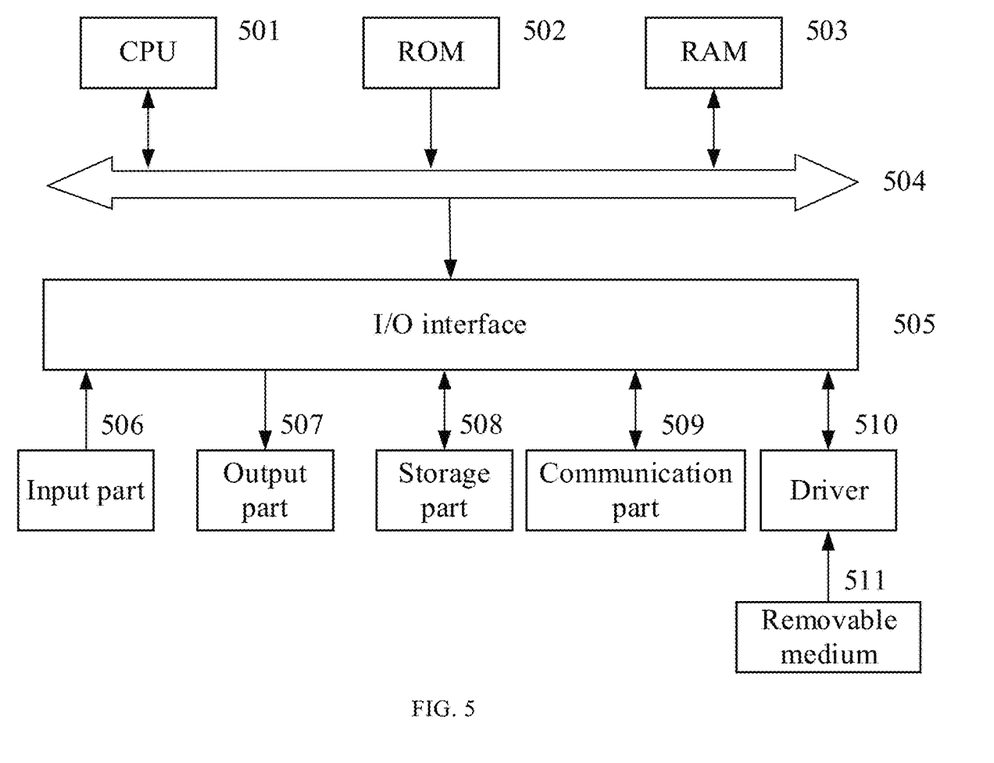
FIG. 5 is a structural diagram of a computer system of an electronic device, suitable for implementing embodiments of the present disclosure, according to an embodiment of the present disclosure.

FIG. 5 is a schematic structural diagram of a computer system of a server suitable for implementing the method and device embodiments of the present disclosure. The server shown in FIG. 5 is merely an example, and should not be conceived as any limitation to the functions and application range of the embodiments of the present disclosure.

As shown in FIG. 5, the computer system includes a central processing unit (CPU) 501, which can perform various suitable actions and processing according to a program stored in a read-only memory (ROM) 502 or a program loaded from a storage part 508 to a random access memory (RAM) 503. The RAM 503 further stores various programs and data required for operations of the system. The CPU 501, the ROM 502, and the RAM 503 are connected to each other through a bus 504. An input/output (I/O) interface 505 is also connected to the bus 504.

The following components are connected to the I/O interface 505: an input part 506 including a keyboard and a mouse; an output part 507 including a cathode-ray tube (CRT), a liquid crystal display (LCD) and a loudspeaker; the storage part 508 including a hard disk; and a communication part 509 including a network interface card such as a local area network (LAN) card or a modem. The communication part 509 executes communication processing via a network such as the Internet. A driver 510 may also be connected to the I/O interface 505 as required. A removable medium 511, such as a magnetic disk, an optical disc, a magneto-optical disc, or a semiconductor memory, is installed on the driver 510 as required, such that a computer program read therefrom can be installed in the storage part 508 as required.

Particularly, according to the embodiments of the present disclosure, the process described above with reference to the flowchart may be implemented as a computer software program. For example, an embodiment of the present disclosure includes a computer program product including a computer program carried by a computer-readable medium. The computer program includes program code for executing the method shown in the flowchart. In this embodiment, the computer program may be downloaded from a network by means of the communication part 509, and/or be downloaded from a removable medium 511. When the computer program is executed by the CPU 501, the functions defined in the method of the present disclosure are executed. It should be noted that, the computer-readable medium in the present disclosure may be a computer-readable signal medium, a computer-readable storage medium, or a combination thereof. The computer readable storage medium, may be, for example, but not limited to, electrical, magnetic, optical, electromagnetic, infrared, or semiconductor systems, apparatuses, or devices, or any combination thereof. More specific examples of the computer-readable storage medium may include, but are not limited to: an electric connector with one or more wires, a portable computer magnetic disk, a hard disk, a RAM, a ROM, an erasable programmable read-only memory (EPROM or flash memory), an optical fiber, a compact disk read-only memory (CD-ROM), an optical storage device, a magnetic storage device, or any proper combination thereof. In the present disclosure, the computer readable storage medium may be any tangible medium including or storing a program, and the program may be used by or used in combination with an instruction execution system, apparatus or device. In the present disclosure, the computer readable signal medium may include a data signal propagated in a baseband or propagated as a part of a carrier, and carries a computer readable program code. The propagated data signal may be in various forms, including but not limited to an electromagnetic signal, an optical signal, or any suitable combination thereof. The computer-readable signal medium may alternatively be any computer-readable medium except the computer-readable storage medium. The computer-readable medium may send, propagate or transmit a program used by or used in combination with an instruction execution system, apparatus or device. The program code contained on the computer readable medium may be transmitted using any suitable medium, including but not limited to: wireless, wire, optical fiber, RF, or any suitable combination thereof.

The computer program code for executing the operations in the present disclosure may be compiled by using one or more program design languages or a combination thereof. The programming languages include object oriented programming languages, such as Java, Smalltalk, and C++, and conventional procedural programming languages, such as C or similar programming languages. The program code may be executed fully on a user computer, executed partially on a user computer, executed as an independent software package, executed partially on a user computer and partially on a remote computer, or executed fully on a remote computer or a server. When a remote computer is involved, the remote computer may be connected to the user computer via any type of network including a LAN or a wide area network (WAN), or may be connected to an external computer (for example, connected via the Internet by using an Internet service provider).

The flowcharts and block diagrams in the accompanying drawings illustrate system architectures, functions and operations that may be implemented by the system, method and computer program product according to the embodiments of the present disclosure. In this regard, each block in the flowcharts or block diagrams may represent a module, a program segment or a part of code, and the module, the program segment or the part of code includes one or more executable instructions for implementing specified logic functions. It should also be noted that, in some alternative implementations, the functions marked in the blocks may alternatively occur in a different order from that marked in the drawings. For example, two successively shown blocks actually may be executed in parallel substantially, or may be executed in reverse order sometimes, depending on the functions involved. It should also be noted that each block in the flowcharts and/or block diagrams and combinations of the blocks in the flowcharts and/or block diagrams may be implemented by a dedicated hardware-based system for executing specified functions or operations, or may be implemented by a combination of dedicated hardware and computer instructions.

Terms such as "first" and "second" are intended to distinguish between similar objects, rather than describe or indicate a specific order or sequence.

Terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present disclosure are described in the preferred implementations with reference to the drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions after these changes or substitutions should fall within the protection scope of the present disclosure.

What is claimed is:

1. A magnetic particle imaging (MPI) and fluorescence molecular tomography (FMT)-fused multimodal imaging system for a small animal, comprising an image processing module, a display module, a control module, an object table, a gradient coil, a driving coil, a reception coil, a fluorescence camera, and a light source module, wherein the gradient coil comprises a first rounded rectangular coil and a second rounded rectangular coil; the first rounded rectangular coil and the second rounded rectangular coil are located on a same horizontal plane that serves as a first horizontal plane; the first rounded rectangular coil and the second rounded rectangular coil are arranged with respective long sides opposite, short sides flush, and axes parallel, and are symmetrically distributed at two sides of a longitudinal axis at a center of the object table; and the gradient coil is configured to construct a static field free line (FFL), such that magnetic particles around the FFL are saturated to form a gradient field in a space;

the driving coil comprises a third rounded rectangular coil, a fourth rounded rectangular coil, and a fifth rounded rectangular coil; the third rounded rectangular coil, the fourth rounded rectangular coil, and the fifth rounded rectangular coil are located on a same horizontal plane that serves as a second horizontal plane; the second horizontal plane is parallel to the first horizontal plane; the third rounded rectangular coil, the fourth rounded rectangular coil, and the fifth rounded rectangular coil are arranged with respective long sides parallel and short sides flush; a center of the third rounded rectangular coil and the center of the object table are located on a same longitudinal axis; the fourth rounded rectangular coil and the fifth rounded rectangular coil are located at two sides of the third rounded rectangular coil, and have a same distance to the third rounded rectangular coil; and the driving coil is configured to counteract a magnetic field of the gradient coil so as to control the FFL to make translational motion;

the reception coil is a circular coil provided directly below the object table and above the gradient coil; and the reception coil is configured to acquire a nonlinear response signal of the magnetic particles;

the fluorescence camera is provided directly above the object table to perform real-time imaging of a target object placed on the object table;

the light source module is fixed at a periphery of a fluorescence lens of the fluorescence camera to control an imaging mode of the fluorescence camera; and the image processing module is configured to process an image acquired by the real-time imaging of the fluorescence camera as a first image, process and reconstruct the nonlinear response signal acquired by the reception coil as a second image, and fuse the first image and the second image to generate a final imaging result.

2. The MPI and FMT-fused multimodal imaging system for the small animal according to claim 1, wherein the MPI and FMT-fused multimodal imaging system for the small animal takes a direction of the longitudinal axis at the center of the object table as a z-direction and a left-right direction of the longitudinal axis at the center of the object table as an x-direction.

3. The MPI and FMT-fused multimodal imaging system for the small animal according to claim 2, wherein a fluorescence acquisition module and the center of the object table are located on a same perpendicular line; and the light source module is a circular light source with a white light source and fluorescent light source integrated imaging mode.

4. The MPI and FMT-fused multimodal imaging system for the small animal according to claim 2, wherein the object table is able to move up and down and rotate in the z-direction.

5. The MPI and FMT-fused multimodal imaging system for the small animal according to claim 2, wherein the gradient coil is configured to construct the static FFL by:
applying currents of equal magnitude and opposite directions to the first rounded rectangular coil and the second rounded rectangular coil.

6. An MPI and FMT-fused multimodal imaging method for a small animal, based on the MPI and FMT-fused multimodal imaging system for the small animal according to claim 1, and comprising:
S100: fixing the target object to the object table, and injecting a magnetic-nano and optical-fused probe into a body of the target object;
S200: applying currents to the gradient coil to generate the static FFL;
S300: applying a high-frequency excitation current to the driving coil, changing a current ratio between the gradient coil and the driving coil, and controlling translation and rotation of the FFL in the space, thereby scan-imaging the target object on the object table;
S400: decoding and reconstructing the nonlinear response signal acquired by the reception coil to generate an MPI cross-sectional image comprising particle concentration information at different depth positions;
S500: performing, by the fluorescence camera, grayscale subtraction between an acquired original fluorescence signal and a previously acquired background signal to generate a fluorescence image of a surface of the target object; and preprocessing the fluorescence image of the surface of the target object through enhancement and denoising to generate a preprocessed fluorescence image;
S600: extracting a position of magnetic particles in the MPI cross-sectional image and concentration information of the magnetic particles at the position; registering, based on a fixed registration reference point, the MPI cross-sectional image into a three-dimensional (3D) grid space of computed tomography (CT) as a prior region for FMT reconstruction; and performing, in the prior region for FMT reconstruction, FMT reconstruction on the preprocessed fluorescence image to acquire a 3D structural fluorescence distribution of a lesion region in the body of the target object; and
S700: assigning the concentration information of the magnetic particles at the position in the MPI cross-sectional image to a grid node of the 3D structural fluorescence distribution, thereby acquiring an image fusion result comprising the 3D fluorescence distribution, the concentration information of the magnetic particles, and a 3D structure.

7. The MPI and FMT-fused multimodal imaging method for the small animal according to claim 6, wherein the operation of preprocessing the fluorescence image of the surface of the target object through enhancement and denoising to generate the preprocessed fluorescence image comprises:
enhancing the fluorescence image of the surface of the target object through a segmented linear grayscale transformation method, and denoising the fluorescence image of the surface of the target object through a bilateral Gaussian filtering method, thereby acquiring a high-contrast fluorescence image as the preprocessed fluorescence image.

8. The MPI and FMT-fused multimodal imaging method for the small animal according to claim 6, wherein the 3D structural fluorescence distribution of the lesion region in the body of the target object is acquired by:

constructing an FMT reconstruction model, and performing reverse solving as follows:

$$AX=\Phi$$

wherein, A denotes a forward system matrix; X denotes a fluorescent molecule distribution to be solved; and $\Phi$ denotes a surface fluorescence signal;

converting the reverse solving problem into a least squares problem:

$$\min_X E(X) = \|AX - \Phi\|_2^2$$

wherein, E(X) denotes an optimization function; and when the least squares problem is solved, due to an ill-conditioned and ill-posed nature of the system matrix A, an L1 norm constraint is added:

$$\min_X E(x) = \|AX - \Phi\|_2^2 + \lambda\|X\|_1$$

wherein, $\lambda$ denotes a regularization parameter; and solving the least squares problem with the L1 norm constraint through an oblique projection matching pursuit method, thereby acquiring the 3D structural fluorescence distribution of the lesion region in the body of the target object.

9. The MPI and FMT-fused multimodal imaging method for the small animal according to claim 8, wherein the operation of solving the least squares problem with the L1 norm constraint through the oblique projection matching pursuit method, thereby acquiring the 3D structural fluorescence distribution of the lesion region in the body of the target object comprises:

performing a pre-selection process: selecting a node with an intensity greater than a set intensity threshold from the surface fluorescence signal $\Phi$; adding the node to a pre-constructed pre-selected set $E_t$; and calculating an oblique projection operator and a complementary projection operator of each node in the pre-selected set;

wherein, the oblique projection operator and the complementary projection operator are expressed as follows:

$$P_{E_t} = A_{E_t} A_{E_t}^+$$

$$P_{E_t}^\perp = I - P_{E_t}$$

wherein $A_{E_t}$ denotes a column corresponding to the pre-selected set $E_t$ in the system matrix A; $A_{E_t}^+$ denotes a pseudo inverse of $A_{E_t}$; $P_{E_t}$ denotes the oblique projection operator in span($A_{E_t}$); $P_{E_t}^\perp$ denotes the complementary projection operator in an orthogonal complementary space of span($A_{E_t}$); and I denotes an identity matrix;

performing a cyclic iteration process: selecting a column with a strongest correlation with a residual of a previous iteration among remaining columns in the system matrix A, and adding a number of the selected column to a support set T, wherein the correlation is calculated by an inner product of the column and the residual; and the support set comprises some column elements that meet a condition in the system matrix, and is set as an empty matrix before a first iteration; and calculating, based on the support set, a temporary solution X and a residual $r^k$:

$$X = (P_{E_t}^\perp A_T)^\dagger) \qquad (1)$$

$$r^k = \Phi - A_T X$$

wherein, $A_T$ denotes an expansion of elements in the system matrix A corresponding to the support set before a current iteration; and exiting the iteration when the residual of the current iteration is less than a preset threshold E; and outputting the temporary solution and the support set for the current iteration.

10. The MPI and FMT-fused multimodal imaging method according to claim 6, wherein the MPI and FMT-fused multimodal imaging system for the small animal takes a direction of the longitudinal axis at the center of the object table as a z-direction and a left-right direction of the longitudinal axis at the center of the object table as an x-direction.

11. The MPI and FMT-fused multimodal imaging method according to claim 10, wherein in the MPI and FMT-fused multimodal imaging system, a fluorescence acquisition module and the center of the object table are located on a same perpendicular line; and the light source module is a circular light source with a white light source and fluorescent light source integrated imaging mode.

12. The MPI and FMT-fused multimodal imaging method according to claim 10, wherein in the MPI and FMT-fused multimodal imaging system, the object table is able to move up and down and rotate in the z-direction.

13. The MPI and FMT-fused multimodal imaging method according to claim 10, wherein in the MPI and FMT-fused multimodal imaging system, the gradient coil is configured to construct the static FFL by:

applying currents of equal magnitude and opposite directions to the first rounded rectangular coil and the second rounded rectangular coil.

* * * * *